US00PP13207P2

(12) United States Plant Patent
Glancy

(10) Patent No.: US PP13,207 P2
(45) Date of Patent: Nov. 12, 2002

(54) PHALAENOPSIS PLANT NAMED (GOLDEN BUDDHA×PEARLIE) 'PINE RIDGE-A'

(75) Inventor: Terry A. Glancy, Homestead, FL (US)

(73) Assignee: Twyford International Inc., Santa Paula, CA (US)

( * ) Notice: Subject to any disclaimer, the term of this patent is extended or adjusted under 35 U.S.C. 154(b) by 22 days.

(21) Appl. No.: 09/895,638

(22) Filed: Jun. 30, 2001

(51) Int. Cl.[7] ..... A01H 5/00
(52) U.S. Cl. ..... Plt./311
(58) Field of Search ..... Plt./311

*Primary Examiner*—Bruce R. Campell
*Assistant Examiner*—Susan B. McCormick
(74) *Attorney, Agent, or Firm*—C. A. Whealy

(57) ABSTRACT

A new and distinct Phalaenopsis Orchid plant named (Golden Buddha×Pearlie) 'Pine Ridge-A' which produces flowers which are pastel yellow with pink centers and orange red labellum. The flowers are carried on short, sturdy, and upright racemes. The flowers are long lasting. The foliage is compact, very dark green, and glossy. Plants of the new cultivar grow quickly to marketable size. The above features combined make the new cultivar particularly well-suited to commercial production and marketing practices.

2 Drawing Sheets

BACKGROUND OF THE INVENTION

The present invention comprises a new and distinct cultivar of Phalaenopsis Orchid, and hereinafter referred to by the cultivar name, (Golden Buddha×Pearlie) 'Pine Ridge-A'. The new cultivar may be marketed under the name Golden Silk.

Phalaenopsis comprises a genus of about 55 species of herbaceous perennials; many of which, or the hybrids thereof, are suitable for cultivation in the home or greenhouse. Phalaenopsis are predominantly epiphytic or rock-dwelling, and are native to tropical Asia, the Malay Archipelago, and Oceania. The species typically have 2-ranked fleshy oblong or elliptic leaves affixed to a short central stem (monopodial growth), which vary in size from 5 to 8 inches to over 2 feet. The leaves may be entirely green or mottled with silver grey.

Phalaenopsis orchids, referred to as 'Moth Orchids' in the horticultural trade, are used as cut flowers for the florist trade, or sold as flowering potted plants for the home or interiorscape.

Phalaenopsis produce upright or pendent lateral flowering racemes, often with many showy flowers which open in succession beginning with the lowermost. The flowers possess three sepals, and three petals, the lateral ones are similar. The lowermost petal, called the labellum, is three-lobed and is often more brightly colored than the other flower segments. Flower colors include various shades of pink, white, yellow, and red-brown.

Phalaenopsis Orchids are typically propagated from seeds. Asexual propagation of Phalaenopsis is often done from off-shoots which frequently arise from the lower bracts of the inflorescence. The resulting plants are detached from the mother plant and planted in a suitable substrate. Phalaenopsis Orchids may also be asexually reproduced by tissue culture.

The new cultivar was discovered by the Inventor within the progeny of a cross of the parent plants listed below that was made in May, 1994. The new cultivar was selected by the Inventors as a flowering plant in a controlled environment in Homestead, Fla. in Apr., 1997.

Since September, 1997, asexual propagation by tissue culture in a laboratory in Sebring, Fla. has been used to increase the number of plants for evaluation and has demonstrated that the unique combination of characteristics as herein disclosed for the new cultivar are firmly fixed and are retained through successive generations of asexual reproduction.

SUMMARY OF THE INVENTION

The following traits have been repeatedly observed and are determined to be basic characteristics of the new cultivar which in combination distinguish this Phalaenopsis as a new and distinct cultivar:

1. Flowers of the new cultivar are pastel yellow in color and centrally marked with pink. The labellum is orange red in color.

2. Inflorescences of the new cultivar are very short, upright and sturdy and require little support, that is, staking.

3. Leaves of the new cultivar are broadly elliptic, relatively short in length, very dark green, and glossy.

4. Plants of new cultivar grow quickly and uniformly.

5. Plants of the new cultivar flower early, producing marketable flowering plants in about 11 months.

Plants of the new cultivar have not been observed under all possible environmental conditions. The phenotype may vary significantly with variations in environment such as temperature, light intensity, and daylength, without however, any change in genotype.

Plants of the new cultivar differ primarily from plants of the parent cultivars in petal and sepal color. Perhaps the closest commercial comparison to the new cultivar can be made to seedling-derived Phalaenopsis Orchids which are heterogeneous genetically, and typically lack uniformity in growth vigor, plant growth habit, and flower quality. Since this reference point has inconsistent characteristics, a direct comparison for (Golden Buddha×Pearlie) 'Pine Ridge-A' is not available. The new cultivar is a single genotype asexually-propagated via tissue culture; thus its combined horticultural characteristics listed above are uniform and predictable.

BRIEF DESCRIPTION OF THE PHOTOGRAPHS

Colors in the photographs may appear different from the color values that appear in the detailed botanical description which more accurately describe the new cultivar.

The photograph on the first sheet comprises a side perspective view of a typical flowering plant of the new cultivar grown in a 15-cm container.

The photograph on the second sheet comprises a close-up view of a typical inflorescence of the new cultivar. The plant depicted in these photographs is the original seedling selection grown for about three years under appropriate growing conditions.

DETAILED BOTANICAL DESCRIPTION

All color references are measured against The Royal Horticultural Society Colour Chart, (1995 edition). Colors and numerical measurements are approximate as plant growth and development depends on horticultural practices such as light level, temperature, water status and fertilization rate, among others, without, however any change in genotype.

Plants used for the description were 1 to 3 years old and grown in 15-cm containers in Homestead, Fla., in a polyethylene-covered greenhouse with day temperatures about 78 to 96° F., night temperatures about 60 to 82° F., and light levels below 1,000 foot-candles. Information for this description was taken during the winter, 2001.

Botanical classification: Phalaenopsis (Golden Buddha× Pearlie) cultivar Pine Ridge-A.

Parentage: Seedling selected from a cross of the following:

*Seed parent.*—Phalaenopsis cultivar Golden Buddha.

*Pollen parent.*—Phalaenopsis cultivar Pearlie.

The name of the cross listed above has not been recorded by The Royal Horticultural Society to date.

Propagation:

*Type.*—Asexual propagation by tissue culture.

*Time to initiate and elongate roots.*—Summer: About 28 days at 82 to 96° F. Winter: About 42 days at 60 to 78° F.

*Time to produce a fully rooted young plant.*—Summer: About 120 days at 82 to 96° F. Winter: About 180 days at 60 to 78° F.

*Root description.*—Very thick, fleshy, and greenish white in color.

Plant description: Under appropriate growing conditions, plants of the new cultivar attain a mature size of about 12 to 15 cm in height and about 30 to 36 cm in width.

Leaf description:

*Form.*—Leaves are elliptic or obovate with obtuse apex and cuneate base; margins, entire. The leaf blade is flat or slightly folded upward from the midrib. The upper leaf surface is very glossy; the lower leaf surface is dull. The leaves are leathery, very stiff, thick, and glabrous.

*Size.*—Leaf blades of a mature-sized plant are about 16 to 20 cm in length and about 7.3 to 9.2 cm in width.

*Veins.*—Veins are sunken within the lamina.

*Color.*—Adaxial surface: Greener than, but closest to 139A. Abaxial surface: Greener than, but closest to 147B.

Flower/inflorescence description:

*Description.*—The sepals and petals are pastel yellow in color, with pink markings at the base. The sepals are elliptic to ovate in shape, the lateral petals are broadly ovate with a rounded apex. The sepals and petals are flat or slightly cupped. The labellum is deeply three-lobed with two prominent callosities at the central junction of the lateral lobes and base of the midlobe. The lateral lobes of the labellum fold upward about the column, the midlobe extends forward and is terminated by two short appendages at the apex. The lateral lobes of the labellum are obovate in shape, the midlobe is triangular. The labellum is orange red in base color with spots and stripes of dark red purple in the center. The callosities are yellow with dark red-purple spots and stripes. The appendages terminating the midlobe are pale yellow to white in color.

*Dimensions.*—Flower: About 8.5 to 9.2 cm wide, about 7.7 to 8.8 cm high. Sepals: About 4.5 to 4.9 cm long, about 3.2 to 3.7 cm wide. Petals: About 4 to 4.5 cm long, about 4.5 to 5 cm wide. Labellum: About 2.5 to 2.7 cm long, about 2 cm wide (not flattened).

*Coloration.*—Sepals: Adaxial surface: 154D to 4D, flushed with 185C to 185D at base. Abaxial surface: 154C to 154D, tinged with much lighter than, but closest to 185D at base. Dorsal sepal margin, 4D. Lateral Petals: Adaxial surface: Yellow, 2D, flushed and speckled with 185C to 185D at base. Abaxial surface: Yellow, 2D; tinged with much lighter than, but closest to 185D at base. Labellum: Adaxial surface: 23C with lighter than, but closest to 185D, marginally. Center of labellum streaked and spotted with 185A to 59A. Appendages at apex of midlobe, 11D to 155D. Callosities: 12C specked with 60A. Abaxial surface: 158D, tinged in center and along margins with 185D.

*Raceme.*—Dimension: The raceme is typically staked upright to a height of about 45 cm from bsae to tip, and about 6 mm in diameter at its midpoint. About 4 to 6 flowers are produced on each raceme. One or two branch spikes, containing 3 to 5 flowers/buds are typically produced. The raceme is 147A tinged with 187A in color.

*Quantity of flowers and time to flower.*—For an untreated plant as depicted in the photograph on the first sheet which is flowering for the 4th time, about 18 flowers and unopened buds are present. Flowering starts about 5 to 8 months after planting 12-week old liners; first time flowering plants produce about 4 to 6 flowers per raceme.

*Flower longevity.*—Individual flowers maintain good substance and coloration for about two months on the plant. Inflorescences are in flower for about 3 to 5 months on the plant.

*Natural flowering season.*—Plants of the new cultivar typically flower during the winter and early spring in Southern Florida.

Reproductive organs: The stamens, style and stigmas are fused into a single short structure called the column, possessing one terminal anther with pollen grains united into a pollinia, which are covered by an anther cap. The stigma is located under the column behind the pollinia. Ovary inferior, three carpels present.

*Column.*—The column is about 1 cm long, about 6.5 mm wide, and 155D in color.

*Pollinia.*—Two oval masses of pollen present, about 1 mm in diameter, and 21A to 21B in color.

*Stigma.*—Concave, sticky rectangular area, under column, about 4 mm by 3 mm in size, and 155D in color.

*Ovary.*—About 1.7 cm long, about 3 mm diameter, and 145C in color.

*Pedicel.*—About 2.3 cm long, about 3 mm in diameter, and lighter than, but closest to 146D in color.

*Seed.*—Seed production has not been observed.

Temperature tolerance: Plants of the new cultivar have been observed to tolerate temperatures from 45 to 105° F.

Disease/pest resistance: Plants of the new cultivar have not been observed to be resistant to pathogens or pests common to Phalaenopsis Orchids.

General observations: Plants of (Golden Buddha×Pearlie) 'Pine-Ridge-A' produce flowers which are pastel yellow with pink centers. The flowers are carried on short, sturdy, and upright racemes. The flowers are long lasting. The foliage is compact, very dark green, and glossy. The plant grows quickly to marketable size.

It is claimed:

1. A new and distinct cultivar of Phalaenopsis Orchid plant named (Golden Buddha×Pearlie) 'Pine Ridge-A', as illustrated and described.

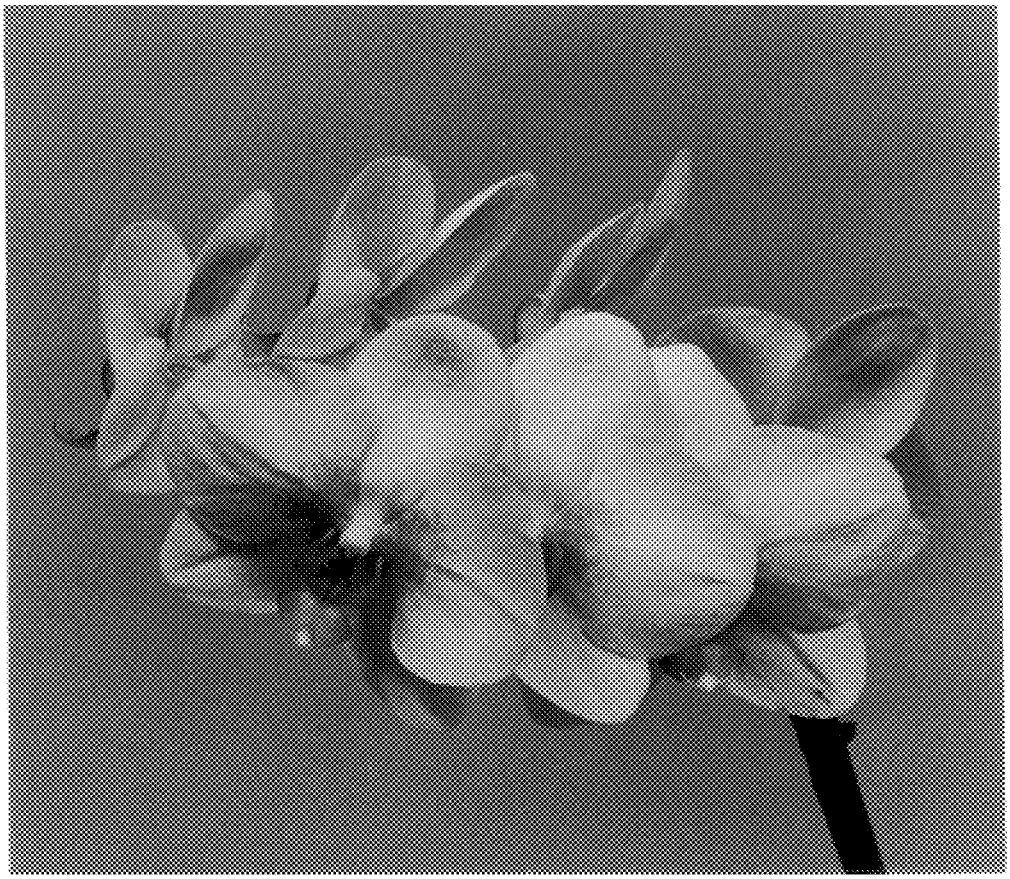

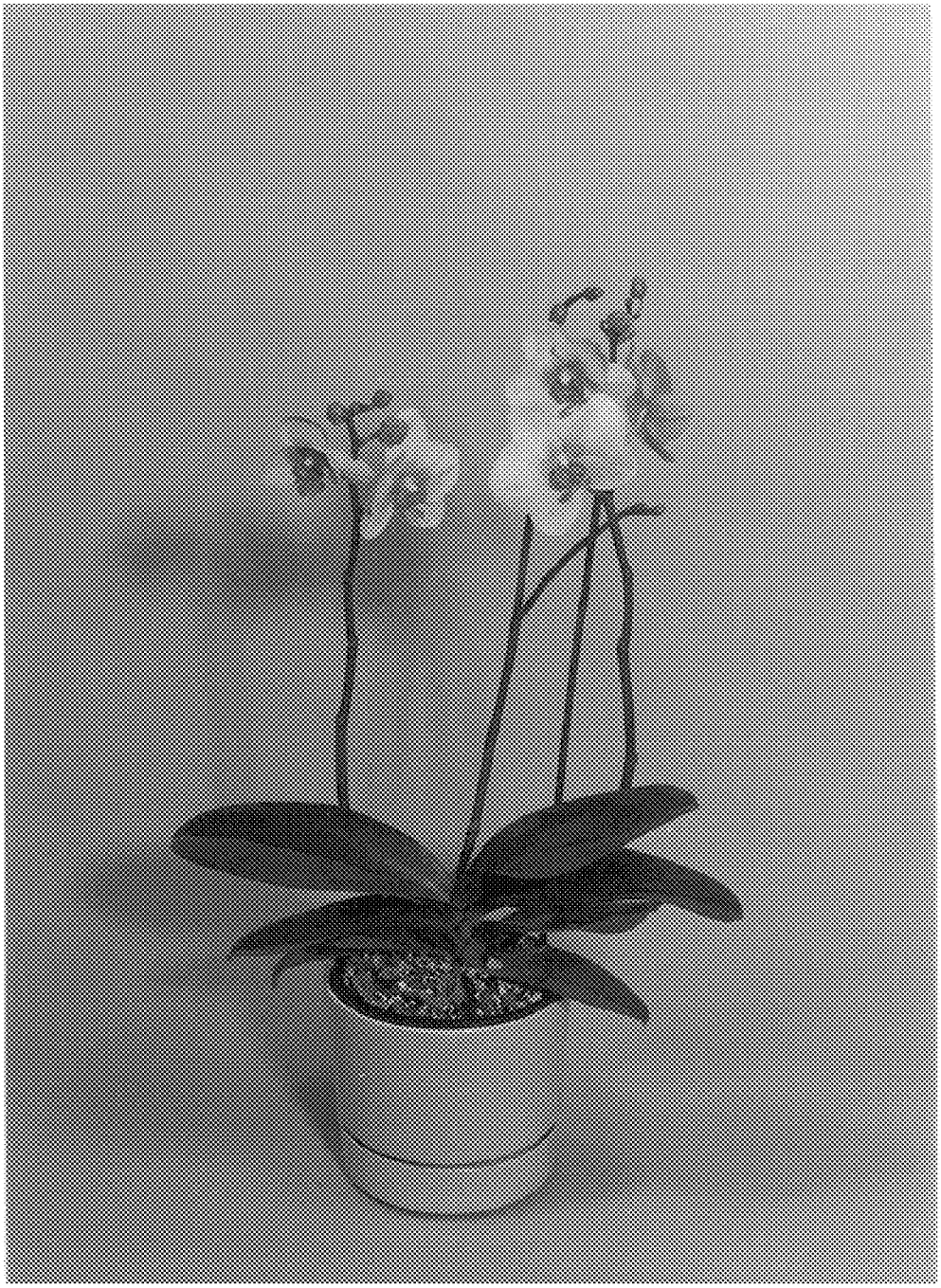

* * * * *